(12) United States Patent
Goss et al.

(10) Patent No.: US 9,012,238 B2
(45) Date of Patent: Apr. 21, 2015

(54) DEVICES FOR SELECTIVE RECRUITMENT, ISOLATION, ACTIVATION, AND/OR ELIMINATION OF VARIOUS CELL POPULATIONS

(75) Inventors: Kendrick Goss, Lexington, MA (US); Carol Gebert, Nahant, MA (US)

(73) Assignee: Biomed Solutions, LLC, Pittsford, NY (US)

( * ) Notice: Subject to any disclaimer, the term of this patent is extended or adjusted under 35 U.S.C. 154(b) by 1875 days.

(21) Appl. No.: 12/223,316

(22) PCT Filed: Jan. 31, 2007

(86) PCT No.: PCT/US2007/002505
§ 371 (c)(1),
(2), (4) Date: Nov. 1, 2010

(87) PCT Pub. No.: WO2007/089762
PCT Pub. Date: Aug. 9, 2007

(65) Prior Publication Data
US 2011/0054347 A1    Mar. 3, 2011

Related U.S. Application Data

(60) Provisional application No. 60/763,351, filed on Jan. 31, 2006.

(51) Int. Cl.
*G01N 33/543* (2006.01)
*A61L 27/38* (2006.01)

(52) U.S. Cl.
CPC .................................. *A61L 27/38* (2013.01)

(58) Field of Classification Search
None
See application file for complete search history.

(56) References Cited

U.S. PATENT DOCUMENTS

| 5,556,765 | A | 9/1996 | Dedolph |
| 6,251,142 | B1 | 6/2001 | Bernacca |
| 6,464,384 | B2 | 10/2002 | Kubera et al. |
| 2001/0034055 | A1 | 10/2001 | Lee et al. |
| 2004/0110290 | A1 | 6/2004 | June et al. |
| 2004/0191246 | A1* | 9/2004 | Connelly et al. ............ 424/140.1 |
| 2009/0253204 | A1* | 10/2009 | King et al. .................... 435/395 |

OTHER PUBLICATIONS

International Search Report and Written Opinion issued Dec. 6, 2007 in corresponding PCT/US2007/02505.

* cited by examiner

*Primary Examiner* — Ann Lam
(74) *Attorney, Agent, or Firm* — Buchanan Ingersoll & Rooney PC

(57) ABSTRACT

Implantable devices comprise at least one or more targeting molecules that form a primary coating layer for selectively recruiting, isolating, activating, and/or eliminating any cells of interest, such as T cells, monocytes, and stem cells. The implantable devices can be utilized for selectively removing a particular subset of cells from bodily fluids of a patient. Various non-selective pharmaceutical agents and biological agents can be incorporated into the implantable devices so that cells of interest can be isolated for elimination or for activation/differentiation. Cell-type selectivity is conferred by the presence of cell-type-specific targeting molecules incorporated into the implantable device, preferably at the surface level to permit direct or indirect interaction between the cells of interest and targeting molecules of the implantable device. Related therapeutic methods for utilizing the implantable devices are also provided. These implantable devices can be manufactured as a stent, a catheter, a holding chamber, or any other device, and can be manufactured into any shape, including a conduit, a vessel, and a tubing.

9 Claims, 12 Drawing Sheets

FIG. 9A
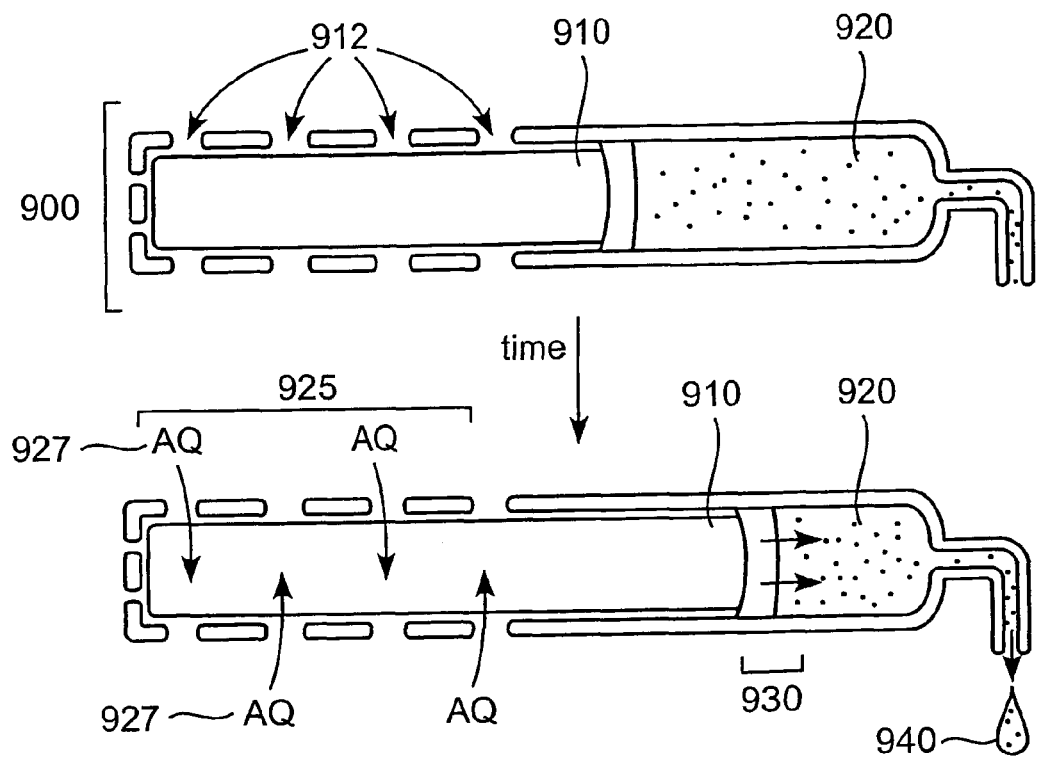
FIG. 9B
FIG. 10
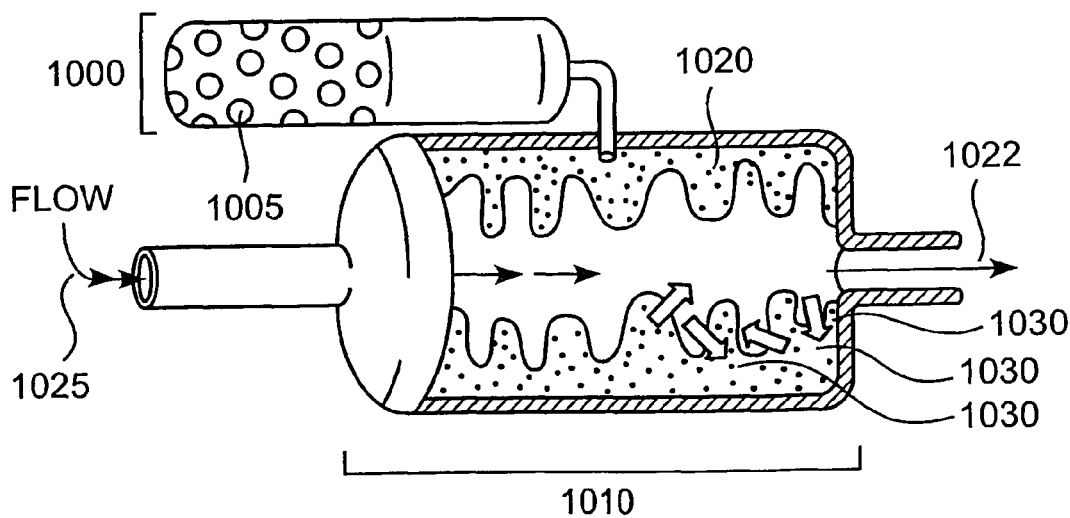

Table 1

| EXAMPLES | A (μm) | B (μm) | C (μm) |
|---|---|---|---|
| I | 500 | 150 | 1000 |
| II | 500 | 150 | 2000 |
| III | 300 | 100 | 500 |
| IV | 300 | 100 | 300 |
| V | 100 | 30 | 50 |

Table 2

| EXAMPLES | D (μm) | E (μm) |
| --- | --- | --- |
| I | 5 | 500 |
| II | 5 | 100 |
| III | 2 | 200 |
| IV | 2 | 75 |

Table 3

| EXAMPLES | F (μm) | G (μm) |
|---|---|---|
| I | 20 | 500 |
| II | 20 | 100 |
| III | 50 | 500 |
| IV | 50 | 200 |

Table 4

| EXAMPLES | H (μm) | J (μm) | K (μm) |
|---|---|---|---|
| I | 500 | 500 | 100 |
| II | 500 | 2000 | 100 |
| III | 200 | 500 | 50 |
| IV | 100 | 75 | 20 |

DEVICES FOR SELECTIVE RECRUITMENT, ISOLATION, ACTIVATION, AND/OR ELIMINATION OF VARIOUS CELL POPULATIONS

CROSS-REFERENCES

This application is a non-provisional application claiming priority to PCT/US2007/002505, filed Jan. 31, 2007, and based on a provisional U.S. Application 60/763,351 filed on Jan. 31, 2006.

TECHNICAL FIELD

The present invention relates to devices that can selectively recruit, sort, preserve, and/or store various cell populations, including T cells, monocytes, and stem cells for various clinical applications.

BACKGROUND OF THE INVENTION

U.S. Pat. No. 5,133,363 entitled "Modular multiple fluid sample preparation assembly" and US2004/0191246A1 entitled "Process for in vivo treatment of specific biological targets in bodily fluid" describe vascular devices that can sort/store biological materials from circulating blood. However, these devices do not describe the recruitment and sequestration of T cells from circulating bodily fluids. T cells are lymphocytes that facilitate the activation of cellular and humoral immunity against various viral, parasitic, and bacterial pathogens that can be recognized as "foreign bodies" or as "non-self," by mature T cells. The maturation/differentiation of T cells occur in the thymus, during which, only mature T cells expressing T-cell receptors having specificity for non-self antigens should emerge from the thymus, whereas any T cells expressing T-cell receptors having high specificity for "self" antigens derived from the host organism should be eliminated from the emerging population of mature T cells. This process for selectively removing auto-reactive T cells occurs by activating apoptotic mechanisms that can cause cellular suicide of such auto-reactive T cells in a process referred to as programmed cell death. Any defect in such self-surveillance mechanisms by genetic aberrations or cellular abnormality that causes the improper emergence of auto-reactive mature T cells from the thymus can lead to the development of various types of autoimmune diseases, including Multiple Sclerosis, Lupus, and rheumatoid arthritis.

SUMMARY OF THE INVENTION

In various embodiments, the implantable devices include at least one chamber coated with one or more targeting molecules for selectively recruiting, isolating, activating, and/or eliminating any cells of interest, such as T cells, monocytes, and stem cells. These implantable devices can be manufactured as a stent, a catheter, a holding chamber, or equivalent devices, and can be manufactured into any shape, including a conduit, a vessel, and a tubing. The implantable devices can be utilized for selectively removing, temporarily or permanently, a particular subset of cells from bodily fluids of a patient. Various non-selective pharmaceutical agents and biological agents can be incorporated into the implantable devices so that cells of interest can be isolated for elimination or for activation/differentiation. Cell-type selectivity is conferred by the presence of cell-type-specific targeting molecules incorporated into the implantable device, preferably at the surface level to permit direct or indirect interaction between the cells of interest and targeting molecules of the implantable device. Related therapeutic methods for utilizing the implantable devices are also provided, including methods for the treatment of cancers, the treatment of auto-immune diseases, the treatment for vascular occlusion, and various stem-cell therapy applications.

BRIEF DESCRIPTION OF DRAWINGS

FIG. 9 is an exemplary osmotic pump, as another embodiment.

FIG. 10 illustrates the exemplary holding chamber of FIG. 4 that further includes a feeding reservoir, as another embodiment.

DETAILED DESCRIPTION OF THE INVENTION

Figure 1:
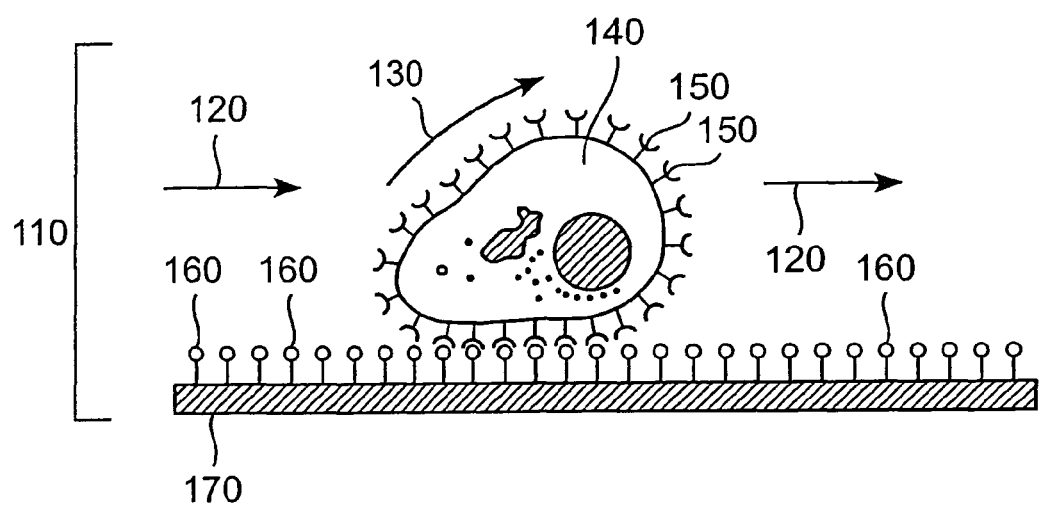
FIG. 1 illustrates an exemplary implantable device comprising targeting molecules that confer cell-type specificity of the implantable device, in which the targeting molecules can be formed as a primary coating layer for the recruitment, isolation, activation, and/or elimination of cells of interest, as one embodiment.

Implantable Devices for Short-Term Retention or Long-Term Storage of Selective Cell Populations In various embodiments, implantable devices comprise at least one chamber coated with one or more targeting molecules for selectively recruiting, isolating, activating, and/or eliminating any cells of interest. Cellular retention within the implantable device is useful for relatively short-term retention of cells (e.g., for cell-sorting applications), such as embodiments described in FIGS. 7 and 8. Cellular retention within the implantable device is useful for relatively long-term storage of cells (e.g., for ex vivo therapy), such as embodiments described in FIGS. 4, 6, and 10.

The implantable devices can be fabricated into any shape, including a vessel, a conduit, or a tube that can be implanted into a patient such that implantable devices can contact any circulating bodily fluid of interest, including blood, lymph fluids, central spinal fluid (CSF), and urine for example. Furthermore, the implantable devices can be useful for controlling the directional flow of bodily fluids. The implantable device can be utilized as an implant or utilized extra-corporeally. Regardless of the actual shape of the implantable device, the implantable device includes at least one chamber for recruiting, isolating, retaining, activating, and/or eliminating the cells of interest.

As used herein, the term "a" that precedes a named article/element refers to one or more of the named article/element. The term "targeting molecule" refers to any molecule that can be incorporated into the contemplated implantable devices, preferably as a surface coating, in which the targeting molecules confers cell-type-specific selectivity of the implantable device. The term "recruitment" refers to any passive or active process for attracting targeted cells of interest to targeting molecules absorbed on the surface of implantable devices of the present invention, and includes various types of physical/chemical/biological interactions, known or unknown, that can occur at the molecular level, such as hydrophobic interactions, hydrophilic interactions, ionic interactions, ligand/receptor interactions, antigen/antibody interactions, and substrate/enzyme interactions. The term "isolation" refers to any process for separating targeted cells of interest from a mixed collection of cells. The term "activation" refers to any process for inducing a biological and/or chemical response within targeted cells of interest, including the activation of intracellular signaling cascades/networks, transcriptional activation, translational activation, and post-transcriptional and post-translational activation processes. The term "elimination" refers to any process for temporarily or permanently removing targeted cells of interest from a mixed collection of cells, in which permanent removal includes cellular death mediated by various cytotoxic agents and cellular suicide by various apoptosis-inducing agents.

A. Implantable Devices for Selective Recruitment, Isolation, Activation, and/or Elimination of T Cells In various embodiments, implantable devices comprise at least one chamber coated with one or more targeting molecules for selectively recruiting, isolating, activating, and/or eliminating T cells of interest. The implantable devices can be utilized for removing a particular subset of T cells of interest from the circulation as a T-cell harvesting device that can be temporarily or permanently implanted into a patient. Specific subset of T cells, such as auto-reactive mature T cells, can be eliminated from the circulation by incorporating nonspecific cytotoxic compounds into the implantable device because cell-type selectivity is conferred by the selection of T-cell-specific targeting molecules incorporated into the implantable device. In preferred embodiments, the implantable device can be manufactured as a stent, a catheter, or any other device coated with one or more T-cell-specific molecules that can selectively recruit, isolate, activate, and/or eliminate T cells within the device.

FIG. 1 illustrates an exemplary implantable device comprising targeting molecules that confer cell-type specificity of the implantable device, in which the targeting molecules can be formed as a primary coating layer for the recruitment, isolation, activation, and/or elimination of cells of interest, as one embodiment. In FIG. 1, the recruitment 110 of a cell of interest 140 to the surface 170 of the implantable device is shown. Suitable cells of interest include various cells of the hematopoietic cell lineage, such as T cells, monocytes, and various stem cells. The surface 170 of the implantable device can be manufactured to adhere various types of "targeting" molecules 160 that can bind sufficiently with high affinity to various cell-surface receptors 150 expressed by cells of interest 140. The cells of interest 140 recruited onto the implantable device can be induced to move 120, with an angular rotation 130, along the surface 170 of the device. Cellular movement across the surface of the implantable device results from the direction and force of fluid flow 120 of aqueous media in the implantable device, and from specific interactions between the cell-surface receptors 150 and the targeting molecules 160 bound to the surface 170 of the implantable device.

A primary coating layer of the implantable device can be utilized for recruiting the attachment of T cells onto the surface of the implantable device, and for manipulating the movement of T cells. For forming the primary coating layer, suitable targeting molecules can be adhered to the surface of the implantable device. Examples of suitable targeting molecules include various molecules that can confer T-cell specificity (i.e., cell-type-specific markers), for example, by recognizing specific epitopes on T-cell receptors and/or other T-cell markers. In one embodiment, suitable targeting molecules include MHC Class I and MHC Class II receptors that can interact specifically with T-cell receptors or other types of cell-surface receptors characteristic of T cells. In other embodiments, implantable devices can be coated with engineered lectin molecules as targeting molecules, as further described in Example 1 provided below. Lectins are glycoproteins produced by vascular epithelium that can interact specifically and non-specifically with hematopoetic cells, including T cells.

Figure 2:
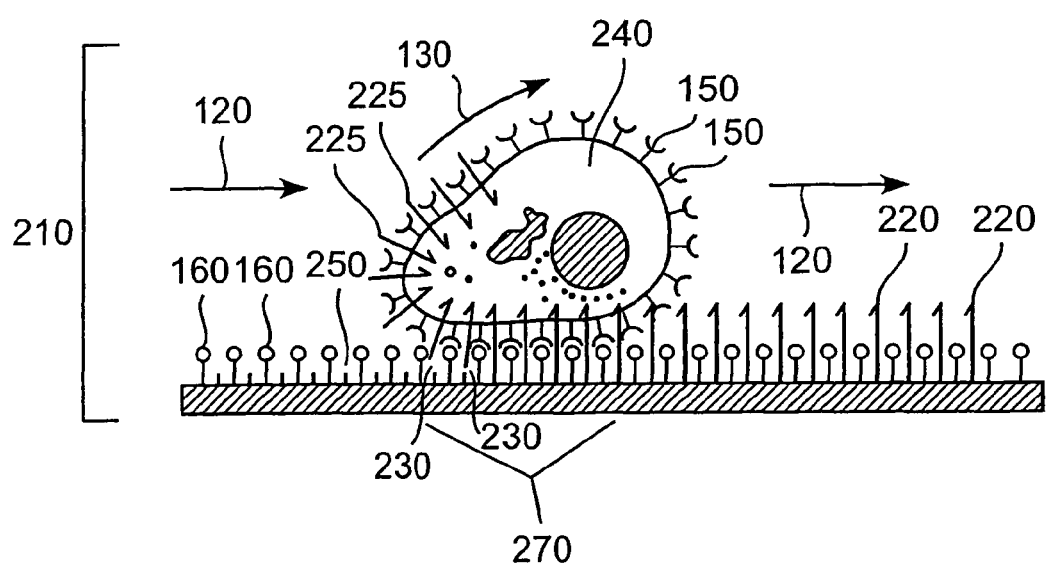
FIG. 2 illustrates an exemplary implantable device comprising various secondary molecules that can be formed as a secondary coating layer, in which the secondary molecules can facilitate the recruitment, isolation, activation, and/or elimination of cells of interest, as another embodiment.
Figure 3:
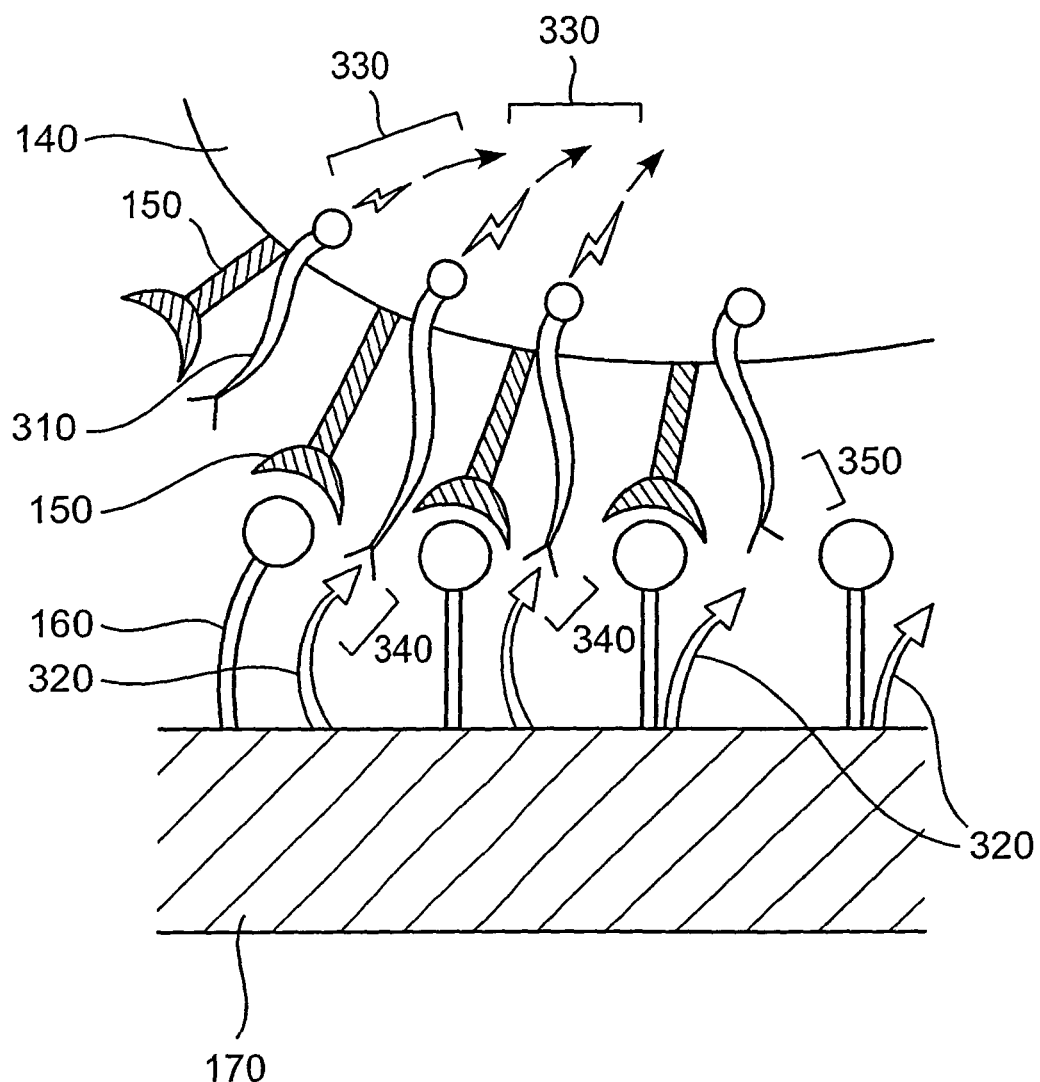
FIG. 3 illustrates the implantable device of FIG. 2, in which Fas ligand molecules (FASL) can be coated onto the surface of the implantable device to induce various cellular responses within recruited cells by activating the Fas receptor (FASR) expressed on the membrane of recruited cells, as another embodiment.

In another embodiment, the implantable device further comprises a secondary coating layer that can be deposited onto the surface of the implantable device and/or superimposed onto the primary coating layer. FIG. 2 illustrates an exemplary implantable device comprising various secondary molecules that can be formed as a secondary coating layer, in which the secondary molecules can facilitate the recruitment, isolation, activation, and/or elimination of cells of interest, as another embodiment. In FIG. 2, the recruitment 210 of a cell of interest 240 to the surface 270 of the implantable device is shown. In addition to the deposition of targeting molecules 160 that can interact with cell-surface receptors 150, various "secondary" molecules 220, such as chemotherapeutic factors, cytokines, or signaling peptides, can be deposited onto the surface 270 of the device in any manner. Certain portions 225 of the secondary molecule 220 can bind strongly to the surface of the cell 140, or can enter the cell by other means. The interaction between cell-surface receptors 150 and targeting molecules 160 can cause cellular movement 120, with an angular rotation 130, under the influence of fluid flow 120 of the aqueous media in the device. Such cellular movement can cause the detachment 230 of the cell from the surface 270 of the device. Molecules, such as 160, 220, can be bound to the surface of the device by various means of attachment, including streptavitin/biotin complex, electrostatic attraction, chemical bonding, mechanical attachment, or other means known to persons skilled in the art. Suitable secondary molecules for forming the secondary coating layer include antiviral drugs, RNAi or siRNA molecules, gamma interferon, other cytokines, and mixtures thereof, that can affect the activity of the recruited T-cells within the implantable device. The secondary coating can be useful in the treatment or prophylaxis of specific diseases, including MS, various autoimmune diseases such as arthritis, and various viral infections.

In a preferred embodiment, the implantable device comprises molecules exhibiting binding activity for HIV-capsid proteins expressed on the surface of HIV-infected T cells, as a primary coating layer. The implantable device can be utilized as a holding vessel to temporarily store harvested HIV-infected T cells that can be permanently removed by extracting the implantable device, or can be utilized as a device delivering cytotoxic compounds incorporated as a secondary coating within the implantable device.

FIG. 3 illustrates the implantable device of FIG. 2, in which Fas ligand molecules (FASL) can be coated onto the surface of the implantable device to induce various cellular responses within recruited cells by activating the Fas receptor (FASR) expressed on the membrane of recruited cells, as another embodiment. In FIG. 3, a Fas receptor 350, in the unactivated state, positioned on the surface of a cell 140 is shown interacting with a Fas ligand on the surface 170 to form a ligand/receptor complex (FASL/FASR) 340. Activation of the FASR induces an intracellular signal 330 that can activate various cellular responses, such as changes in gene expression, activation of programmed cell death, and cytokine production.

B. Implantable Devices for Selective Recruitment, Isolation, Activation, and/or Elimination of Monocytes In various embodiments, implantable devices comprise at least one chamber coated with one or more targeting molecules for selectively recruiting, isolating, activating, and/or eliminating monocytes of interest. The implantable devices can be utilized for removing monocytes from the circulation as a monocyte-harvesting device that can be temporarily or permanently implanted into a patient. Specific subset of monocytes can be eliminated from the circulation by incorporating nonspecific cytotoxic compounds into the implantable device because cell-type selectivity is conferred by the selection of monocyte-specific targeting molecules incorporated into the implantable device. In a preferred embodiment, the implantable device can be manufactured as a stent, a catheter, or any other device coated with one or more monocyte-specific molecules that can selectively recruit, isolate, activate, and/or eliminate monocytes within the device.

A primary coating layer of the implantable device can be utilized for recruiting the attachment of monocytes onto the surface of the implantable device, and for manipulating the movement of monocytes. For forming the primary coating layer, suitable targeting molecules can be adhered to the surface of the implantable device. Examples of suitable targeting molecules include various molecules exhibiting monocyte specificity by recognizing monocyte-specific markers (i.e., cell-type-specific markers). In one embodiment, suitable targeting molecules include monocyte-specific receptors, antibodies, or other binding molecules that can selectively capture, reduce cellular movement, and/or manipulate monocyte movement within the implantable device. In other embodiments, implantable devices can be coated with engineered lectin molecules as targeting molecules, as further described in Example 1 provided below. Lectins are glycoproteins produced by vascular epithelium that can interact specifically and non-specifically with hematopoetic cells, including monocytes.

In another embodiment, the implantable device further comprises a secondary coating layer that can be deposited onto the surface of the implantable device and/or superimposed onto the primary coating layer. In addition to the deposition of targeting molecules that can interact with cell-surface receptors expressed by monocytes, various "secondary" molecules that can be deposited onto the surface of the device in any manner. Targeting molecules can be bound to the surface of the device by various means of attachment, including streptavitin/biotin complex, electrostatic attraction, chemical bonding, mechanical attachment, or other means known to persons skilled in the art. Suitable secondary molecules for forming the secondary coating layer include antiviral drugs, RNAi or siRNA molecules, gamma interferon, other cytokines, and mixtures thereof, that can affect the activity of the recruited monocytes within the implantable device. The secondary coating can be useful in the treatment or prophylaxis of diseases involving improper monocyte differentiation. Monocytes are capable of extensive differentiation following maturation, and the differentiation process can produce a diverse subpopulation of monocytes.

C. Implantable Devices for Selective Recruitment, Isolation, Activation, and/or Elimination of Stem Cells In various embodiments, implantable devices comprise at least one chamber coated with one or more targeting molecules for selectively recruiting, isolating, activating, and/or eliminating stem cells of interest. The implantable devices can be utilized to remove a subset of stem cells of interest from the circulation as a stem cell-harvesting device that can be temporarily or permanently implanted into a patient. Specific subsets of stem cells can be eliminated from the circulation by incorporating cytotoxic compounds into the implantable device because cell-type specificity is conferred by the selection of stem-cell-specific targeting molecules incorporated into the implantable device. In a preferred embodiment, the implantable device can be manufactured as a stent, a catheter, or any other device coated with one or more stem cell-specific molecules that can selectively recruit, isolate, activate, and/or eliminate stem cells within the device.

A primary coating layer of the implantable device can be utilized for recruiting the attachment of stem cells onto the surface of the implantable device and for manipulating the movement of stem cells. For forming the primary coating layer, suitable targeting molecules can be adhered to the surface of the implantable device. Examples of suitable targeting molecules include various molecules exhibiting stem-cell specificity by recognizing stem cell-specific markers (i.e., cell-type-specific markers). In one embodiment, suitable targeting molecules include stem cell-specific receptors, antibodies, or other binding molecules that can selectively capture, reduce cellular movement, and/or manipulate stem cell movement within the implantable device. In other embodiments, implantable devices can be coated with engineered lectin molecules as targeting molecules, as further described in Example 1 provided below. Lectins are glycoproteins produced by vascular epithelium that can interact specifically and non-specifically with hematopoetic cells, including stem cells.

In another embodiment, the implantable device further comprises a secondary coating layer that can be deposited onto the surface of the implantable device and/or superimposed onto the primary coating layer. In addition to the deposition of targeting molecules that can interact with cell-surface receptors expressed by stem cell, various "secondary" molecules that can be deposited onto the surface of the device in any manner. Targeting molecules can be bound to the surface of the device by various means of attachment, including streptavitin/biotin complex, electrostatic attraction, chemical bonding, mechanical attachment, or other means known to persons skilled in the art. Suitable secondary molecules for forming the secondary coating layer include antiviral drugs, RNAi or siRNA molecules, gamma interferon, other cytokines, and mixtures thereof, that can affect the activity of the recruited stem cell within the implantable device.

In various embodiments, the contemplated devices can be utilized for isolating, sorting, storing, and/or culturing stem cells obtained from amniotic fluids ("Isolation of amniotic stem cell lines with potential for therapy," Coppi et al. Nature Biotechnology (1007) Vol. 25:100-106). Selectins are a family of transmembrane molecules, expressed on the surface of leukocytes and activated endothelial cells. The utilization of selectins as targeting molecules is preferred over other known methods, such as centrifugation or antibody-based methods, in that these methods can induce more stress onto stem cells during manipulation. During inflammation, the initial attachment of leukocytes from the blood stream is mediated by members of the selectin family, and can cause a slow downstream movement of leukocytes along the endothelium via adhesive interactions referred to as leukocyte rolling. At least three selectins have been identified. L-selectin is the smallest of the vascular selectins, and can be found on most leukocytes. P-selectin is the largest selectin, and is expressed primarily on activated platelets and endothelial cells. E-selectin is expressed on activated endothelium with chemically or cytokine-induced inflammation. L-selectins, P-selectins, and/or E-selectins in any combination can be incorporated into various implantable devices, including a conduit, a tubing, a matrix, a bead-packed column, and an absorbent fibrous material.

In another embodiment, a cell-isolating apparatus comprises at least one chamber coated with selectins as targeting molecules. In another embodiment, a method, for isolating stem cells contained in an amniotic fluid, comprises contacting an amniotic fluid with a cell-isolating apparatus comprising at least one chamber coated with selectins as target molecules.

In another embodiment, a cell-sorting apparatus comprises at least one chamber coated with selectins. In another embodiment, a method, for sorting stem cells contained in an amniotic fluid, comprises contacting an amniotic fluid with a cell-sorting apparatus comprising at least one chamber coated with selectins as target molecules.

In another embodiment, a cell-storage apparatus comprises at least one chamber coated with selectins. In another embodiment, a method, for storing stem cells contained in an amniotic fluid, comprises contacting an amniotic fluid with a cell-storing apparatus comprising at least one chamber coated with selectins as target molecules.

In another embodiment, a cell-culture apparatus comprises at least one chamber coated with selectins. In another embodiment, a method, for culturing stem cells contained in an amniotic fluid, comprises contacting an amniotic fluid with a cell-culture apparatus comprising at least one chamber coated with selectins as target molecules.

D. Implantable Devices for Selective Recruitment, Isolation, and/or Activation of Lymphocytes to Promote Vaccination of Host Organism against Various Pathogens In a preferred embodiment, the implantable device comprises at least one chamber coated with an antigen derived from a pathogen, wherein the surface of the implantable device presents the antigen molecules to lymphocytes circulating within a bodily fluid. In another preferred embodiment, the implantable device comprises a coating layer that includes MHC Class I molecules complexed with one or more antigen molecules derived from a pathogen, in which the surface of the implantable device can present the antigen molecules to lymphocytes circulating within a bodily fluid. The antigen molecules of interest include any molecule derived from a pathogen (e.g., virus, parasite, bacteria) that can illicit an immune response if administered systemically. The implantable device can be utilized for sensitizing or "priming" a patient to various pathogens prior to actual pathogenic exposure so that in the event of actual exposure, the host organism will be able to mount a robust immune response against the pathogen.

Figure 4:
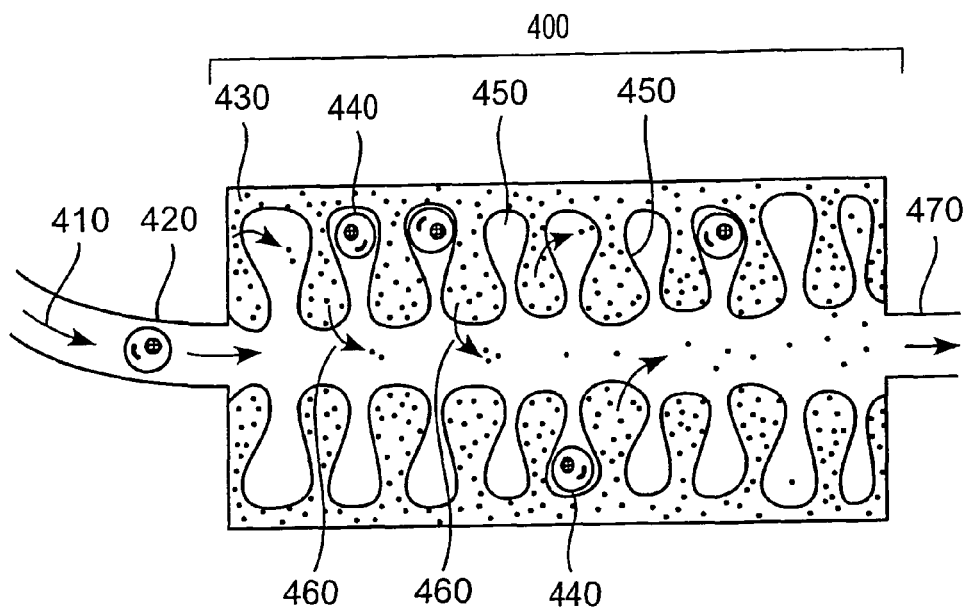
FIG. 4 illustrates an exemplary holding chamber for storing cells of interest, as another embodiment.

E. An Implantable Holding Chamber for Selective Storage/Growth of Cells of Interest FIG. 4 illustrates an exemplary holding chamber for storing cells of interest, as another embodiment. In FIG. 4, a cross-sectional view of a holding chamber 400 for selectively sorting and isolating cells of interest from circulating fluids is shown. The holding chamber 400 can be connected to a catheter 420, which can be connected to a circulating fluid of a patient. Fluids from a patient that enters through the catheter 420 can flow into the holding chamber from the anterior end of the device, can pass through the device in a direction 410, and can exit 470 the device at the posterior end. The holding chamber can include a membrane 450 composed of an osmotically active membrane that can be configured to have substantial surface area (i.e., invaginations) in order to create microenvironments that can support the attachment/recruitment/growth of cells of interest 440 that enter the holding chamber in the presence of suitable growth media 430 that can be provided. Such growth media 430 can be supplemented with various compounds 430, including signaling molecules, nutrients, and/or drugs, and can be transferred into the interior of the holding chamber 400.

Figure 6:
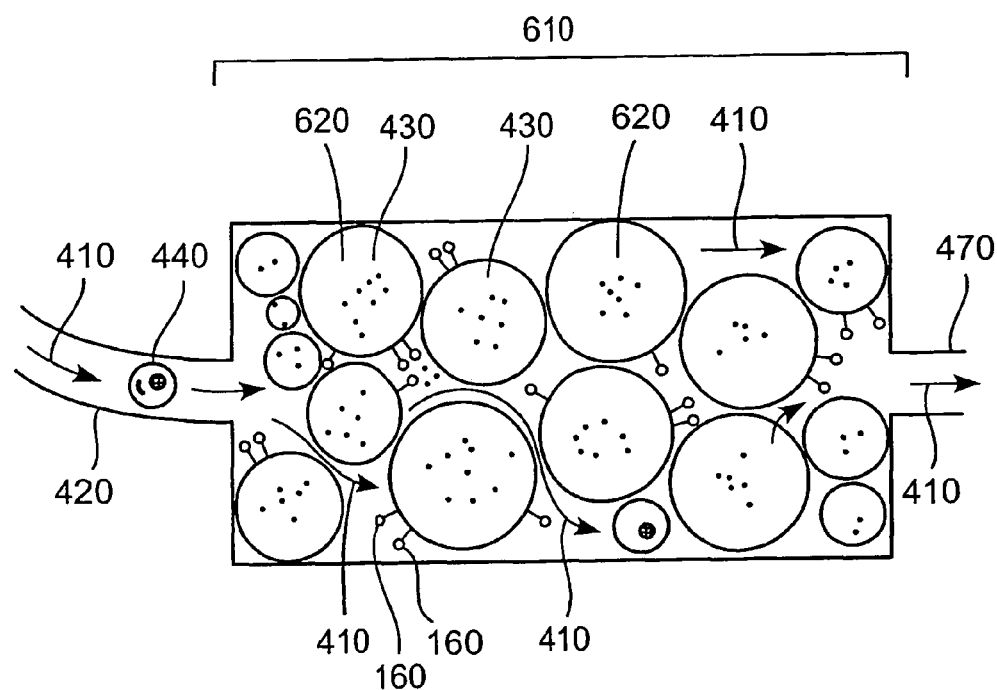
FIG. 6 illustrates the holding chamber of FIG. 4, further comprising osmotically active beads containing compounds of interest, as another embodiment.

FIG. 6 illustrates the exemplary holding chamber of FIG. 4, further comprising osmotically active beads containing compounds of interest, as another embodiment. In FIG. 6, the holding chamber includes osmotically active beads, such as bead 620, containing various compounds of interest 430, including signaling molecules, nutrients, and/or drugs. Cells 440 that enter the holding chamber can move through the microenvironments created by the stacked beads, and can interact with the surface of the beads by binding to receptor molecules 160 deposited on the surface of the beads or by binding soluble molecules 430 diffusing from the beads 620.

FIG. 10 illustrates the exemplary holding chamber of FIG. 4 that further includes a feeding reservoir, as another embodiment. In FIG. 10, a cross-sectional view of a cell holding chamber 1010 for selectively sorting and isolating cells of interest from circulating fluids is shown. The holding chamber 1010 can be connected to a catheter, which can be connected to a circulating fluid of a patient. Fluids from a patient that enters through the catheter can flow into the holding chamber 1010 from the anterior end of the device 1025, can pass through the holding chamber 1010, and can exit 1027 the device at the posterior end. The holding chamber can include a membrane composed of an osmotically active membrane that can be configured to have substantial surface area (i.e., invaginations) in order to create microenvironments that can support the attachment/recruitment/growth of cells of interest that enter the holding chamber in the presence of suitable growth media 1005 that can be provided by attaching one or more feeding reservoir 1000 to the holding chamber 1010. Such growth media 1005 can be supplemented with various compounds, including signaling molecules, nutrients, and/or drugs, and can be transferred into the interior of the holding chamber 1010. Such compounds can diffuse 1030 from one section of the holding chamber into another.

Cells suitable for storing/growing within holding chambers illustrated in FIGS. 4, 6, and 10 include undifferentiated stem cells having pluripotency to develop into cells of different lineages. The holding chambers can be implanted within a patient and connected to a device that can harvest cells out of the bloodstream or other bodily fluids. In another embodiment, the holding chamber includes beads that can elute nutrients and/or signaling molecules to cells adhered to the surface of beads. Signalizing molecules can cause cells to differentiate along a particular lineage. In another embodiment, cells can be expelled from the implantable holding chamber with fluids sourced from an implanted supply chamber that can be activated and powered by the osmotic pressure of a patient's own fluids. In another embodiment, the implanted supply chamber is replenishable by an external source, in which the cells can be expelled transdermally for recovery, back to the patient's bodily fluids. The expulsion force can be provided by an external pressure, by actuation of an implanted motor, by mechanical movement of a patient's body (e.g. muscle traction).

Figure 12:
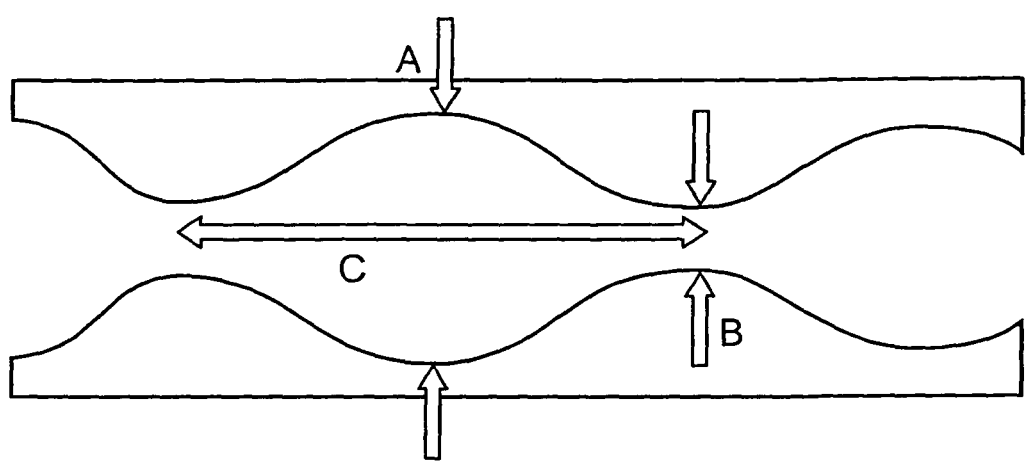
FIG. 12 is a cross-sectional diagram of an exemplary configuration for designing a tubing, in which the tubing can be configured to form a conduit having an inner diameter that varies in a pattern along the length of the tubing, as another embodiment.

F. Exemplary Configurations for Manufacturing Various Tubing Devices for Selective Recruitment, Isolation, Activation and/or Elimination of Cells of Interest FIG. 12 is a cross-sectional diagram of an exemplary configuration for designing a tubing, in which the tubing can be configured to form a conduit having an inner diameter that varies in a pattern along the length of the tubing, as another embodiment. In FIG. 12, a longitudinal cross-section of a tubing is shown comprising a suitable material, such as polypropylene or polyethylene glycol. The tubing can be configured to form a conduit having an inner diameter that can vary in a regular or irregular pattern along the length of the tubing. Parameter A represents thickness of the tubing wall to form maximal inner diameter of the tubing. Parameter B represents the thickness of the tubing wall to form minimal inner diameter of the tubing. Parameter C represents the length of tubing between two sections of tubing with minimal inner diameters. Dimensional parameters (A, B, and C) of the tubing device can be selected to improve the effectiveness of the tubing device for sorting, capturing, and/or manipulating cells of interest. Table 1 provides a tube variant table listing 5 examples of possible combinations of parameters A, B, and C. Parameter A can range from about 20 μM to about 1000 μM, parameter B can range from about 20 μM to about 1000 μM, and parameter C from about 10 μM to about 2000 μM. Regular or irregular values for parameters A, B, and C can occur for each iteration of the repeating configuration pattern along the length of the tube. This tubing device can be utilized as a conduit for transporting various bodily fluids as described herein. In various embodiments, the tubing device can be coated with various molecules described herein for forming a primary and/or secondary coating layers.

Figure 13:
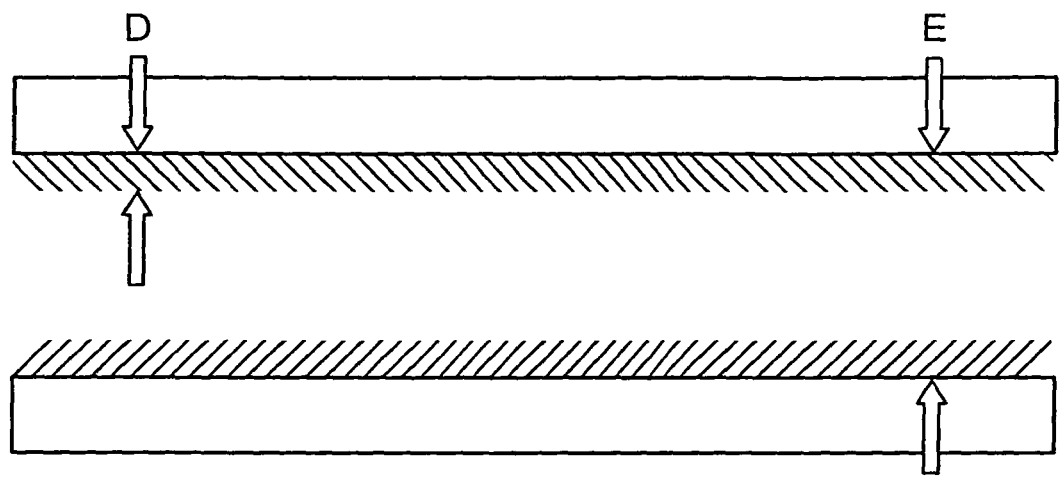
FIG. 13 is a cross-sectional diagram of an exemplary configuration for designing a tubing, in which the tubing can be configured to include multiple "fibrous" extensions that form the interior lining of the tube, as another embodiment.

FIG. 13 is a cross-sectional diagram of an exemplary configuration for designing a tubing, in which the tubing can be configured to include multiple "fibrous" extensions that form the interior lining of the tube, as another embodiment. In FIG. 13, a longitudinal cross-section of a tubing is shown comprising a suitable material, such as polypropylene or polyethylene glycol. The tubing can be configured to include multiple "fibrous" extensions that form the interior lining of the tube. In one embodiment, the fibrous extensions can be covalently bound to the interior surface of the tubing. In another embodiment, the fibrous extensions can be attached through ionic interactions. These fibrous extensions can be deposited in conjunction with various coatings described herein. Parameter D represents the inner diameter of the tubing. Parameter E represents the inner diameter of the tubing. Dimensional parameters (D and E) of the tubing device can be selected to improve the effectiveness of the tubing device for sorting, capturing, and/or manipulating cells of interest. Table 2 provides a tube variant table listing 4 examples of possible combinations of parameters D and E. Parameter D can range from about 2 μM to about 50 μM, and parameter E can range from about 20 μM to about 2000 μM. Regular or irregular values for parameters D and E can occur for each iteration of the repeating configuration pattern along the length of the tube. In another embodiment, selective sections of the tubing can be configured to include fibrous extensions of variable lengths, as "patches" or "stripes," along the inner surface of the tubing. This tubing device can be utilized as a conduit for transporting various bodily fluids as described herein. In various embodiments, the tubing device can be coated with various molecules described herein for forming a primary and/or secondary coating layers.

Figure 14:
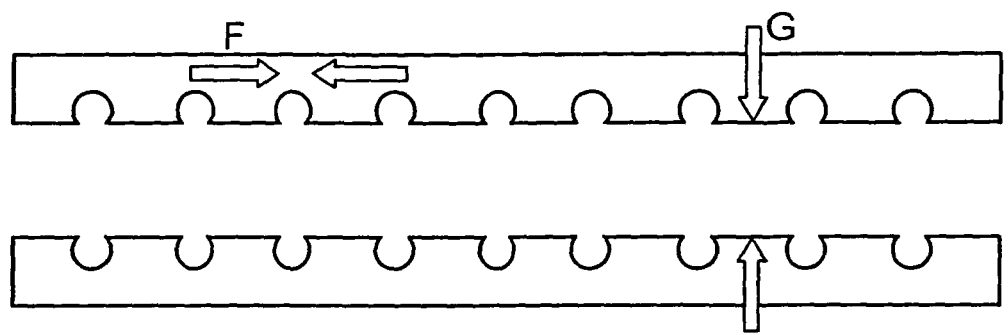
FIG. 14 is a cross-sectional diagram of an exemplary configuration for designing a tubing, in which the tubing can be configured to include multiple pits along the inner surface of the tubing, as another embodiment.

FIG. 14 is a cross-sectional diagram of an exemplary configuration for designing a tubing, in which the tubing can be configured to include multiple pits along the inner surface of the tubing, as another embodiment. In FIG. 13, a longitudinal cross-section of a tubing is shown comprising a suitable material, such as polypropylene or polyethylene glycol. The tubing can be configured to include multiple pits along the inner surface of the tubing. Parameter F represent the average diameter of a pit, and parameter G represents the inner diameter of the tubing. Dimensional parameters (F and G) of the tubing device can be selected to improve the effectiveness of the tubing device for sorting, capturing, and/or manipulating cells of interest. Table 3 provides a tube variant table listing 4 examples of possible combinations of parameters F and G. Parameter F can range from about 20 μM to about 1000 μM. Parameter E can range from about 20 μM to about 1000 μM. Regular or irregular values for parameters F and G can occur for each iteration of the repeating configuration pattern along the length of the tube. This tubing device can be utilized as a conduit for transporting various bodily fluids as described herein. In various embodiments, the tubing device can be coated with various molecules described herein for forming a primary and/or secondary coating layers. In another embodiment, the pits can be coated with molecules different from molecules selected to coat the inside surface of the tubing, in the non-pit regions.

Figure 15A:
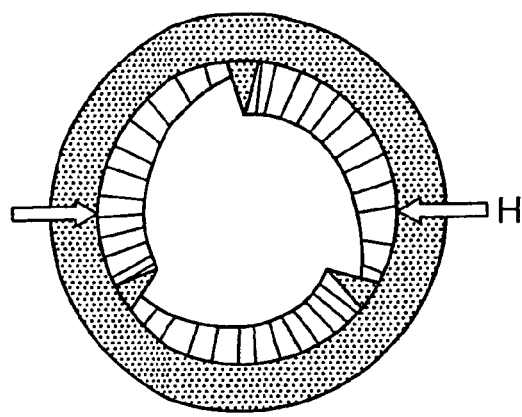
FIG. 15 is a cross-sectional diagram of an exemplary configuration for designing a tubing, in which the tubing can be configured to include multiple rifling grooves along the inner surface of the tubing, as another embodiment.
Figure 15B:
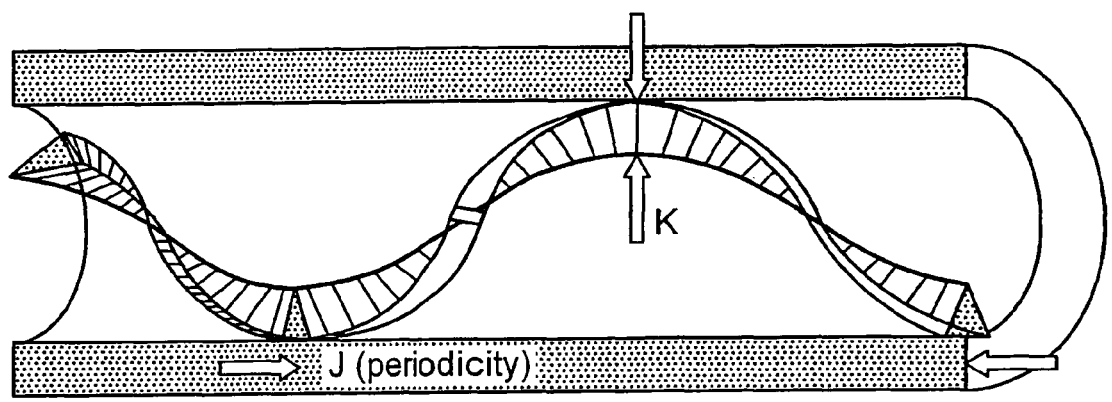

FIG. 15 is a cross-sectional diagram of an exemplary configuration for designing a tubing, in which the tubing can be configured to include multiple rifling grooves along the inner surface of the tubing, as another embodiment. FIG. 15A illustrates a cross-section of a tubing comprising a suitable material, such as polypropylene or polyethylene glycol. FIG. 15B illustrates a longitudinal cross-section of the tubing illustrated in FIG. 15A. In FIGS. 15A and 15B, the tubing can be configured to include multiple rifling grooves along the inner surface of the tubing. Parameter H represents the inner diameter of the tubing. Parameter K represents the depth of the rifling groove. Parameter J represents the periodicity of the rotation/twist of a rifling groove. Dimensional parameters (H, J, and K) of the tubing device can be selected to improve the effectiveness of the tubing device for sorting, capturing, and/ or manipulating cells of interest. Table 4 provides a tube variant table listing 4 examples of possible combinations of parameters H, J, and K. Parameter K can range from about 2 μM to about 500 μM. Parameter H can range from about 20 μM to about 2000 μM. Parameter J can range from about 20 μM to about 20,000 μM. Regular or irregular values for parameters (H, J, and K) can occur for each iteration of the repeating configuration pattern along the length of the tube. This tubing device can be utilized as a conduit for transporting various bodily fluids as described herein. In various embodiments, the tubing device can be coated with various molecules described herein for forming a primary and/or secondary coating layers. In another embodiment, the rifling grooves can be coated with molecules different from molecules selected to coat the inside surface of the tubing.

Figure 5:
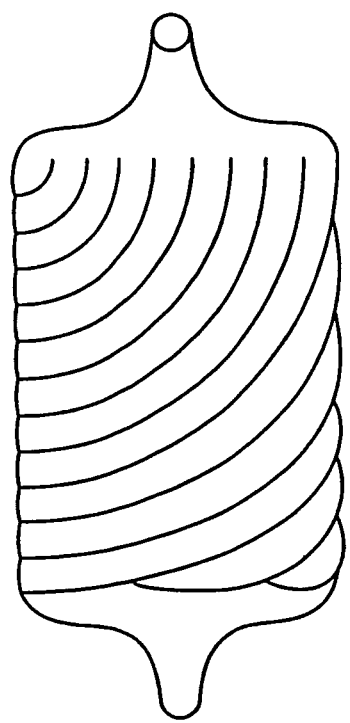
FIG. 5 is a cross-sectional diagram of a bundle of tubes illustrated in FIGS. 12-15, as another embodiment.

FIG. 5 is a cross-sectional diagram of a bundle of tubes illustrated in FIGS. 12-15, as another embodiment. In FIG. 5, a bundle of multiple tubes in a manifold form is shown, which can be assembled by gathering the tubes together at the ends to provide a common entry and a common exit for all tubes of the bundle. In one embodiment, fluids from a single common source can be passed into all tubes of the bundle, which can be configured either to allow the fluid from all tubes to exit via a common mechanism, or to permit fluids to exit individual tubes via different mechanisms. In another embodiment, fluids from multiple different sources can be passed into the tubes of the bundle, which can be configured either to allow the fluid from all tubes to exit via a common mechanism, or to permit fluids to exit individual tubes via different mechanisms.

G. Stents Assembled as a Liquid or a Semi-Liquid Polymer

Vascular stents have been developed to overcome a condition referred to as "restenosis," in which smooth muscle cells from the vascular epithelium progressively grow into the lumen of the stent, resulting in a larger vessel occlusion than that which existed preoperatively. To overcome this problem, experimental stents have been coated with various cytotoxic compounds capable of preventing this re-growth. Despite observable cell growth inhibition activity, the supply of cytotoxic drug can deplete over time resulting in invasive re-growth. Current vascular stents cannot be removed without the trauma of surgical intervention. In some cases, stent removal is not impossible due to restenosis.

Figure 11A:
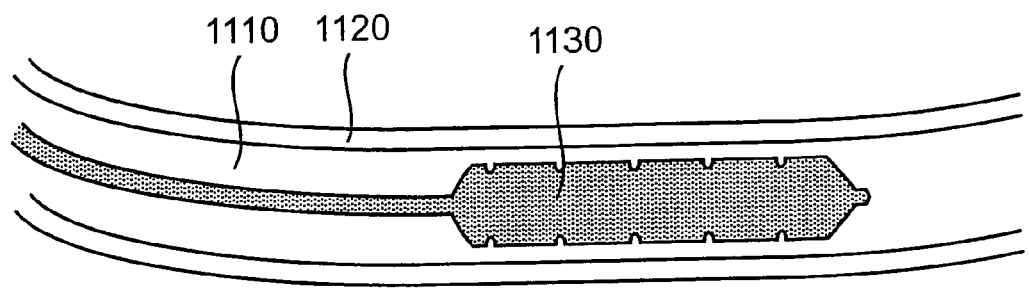
FIGS. 11A-D illustrate an exemplary dissolvable stent for opening vascular occlusions, as another embodiment.
Figure 11B:
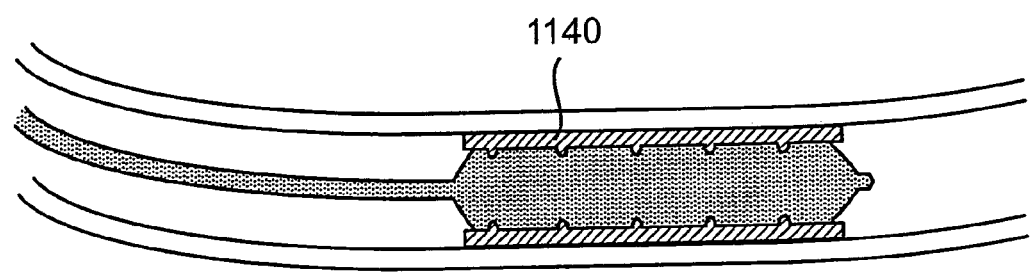
Figure 11C:
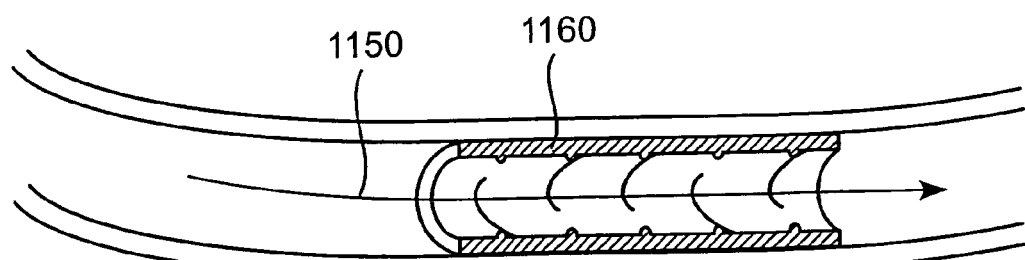
Figure 11D:
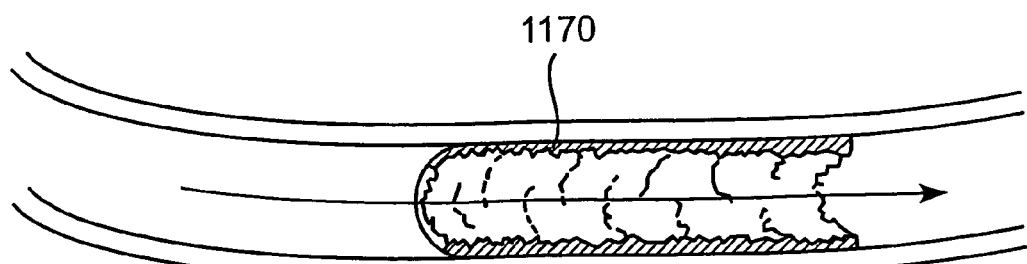

FIGS. 11A-D illustrate an exemplary dissolvable stent for opening vascular occlusions, as another embodiment. In FIG. 11A, a catheter 1110 attached to a balloon 1130 in a deflated state can be inserted into an occluded blood vessel 1120, and subsequently inflated to expand the diameter of the occluded blood vessel to reverse the occlusion. In FIG. 11B, a semi-liquid polymer 1140 can be deposited near the balloon 1130 end of the catheter. The semi-liquid polymer 1140 can be expelled out from the catheter balloon 1130 so that the semi-liquid polymer 1140 hardens as a ring-like structure in situ, conforming to the shape and size of the opened vessel, and thereby, forming a stent. In FIG. 11C, the stent 1160 remains in place after the removal of the catheter 1110 so that normal blood flow can pass 1150 through the stent 1160. In FIG. 11D, a newly exposed surface of a stent 1170 comprising a dissolvable polymer is formed as the semi-liquid polymer progressively dissolves into the circulation over time.

Suitable material for manufacturing vascular stents, described in FIGS. 11A-D, include various types of metals and plastic polymers. In one embodiment, a vascular stent comprises a semi-liquid polymer that can solidify in place, once delivered to the vessel of interest. A stent-delivering catheter can be expanded within the vessel in order to physically change the shape of the vessel, thereby improving blood flow. The polymer stent catheter operates in a similar way, however, once this expansion takes place, the polymer can be forced out of holes of the catheter, and forced into spaces between the expanded catheter tip and the vessel wall. Once exposed to the local environment, and in contact with the vessel wall, the polymer can harden (in response to temperature, pH, ion concentration, or other means) in order to form a tube that can conform to the shape of the vessel. Since the stent tube is a solid structure, unlike current stents, restenosis is not likely to develop since entry into the lumen of the stent cannot occur.

Vascular stents can be introduced into a vascular setting in a compressed state by any means, for example, supported by a catheter. The catheter can be inserted into a vessel of interest, and allowed to expand into place so that the vessel can be held open, or widen, in order to increase vascular space for enabling more efficient blood flow. Although the vascular stents contemplated are solid in structure, however, the vascular stent is not a static structure because the material composing the vascular stent is dissolvable. This affords many advantages, including the maintenance of the local environment inside the stent, and the release of drugs at a constant rate. In one embodiment, the vascular stents comprising a dissolvable polymer further comprises one or more cytotoxic drugs, thereby preventing the invasion of smooth muscle cell by restenosis. In another embodiment, the vascular stents comprising a dissolvable polymer further comprises one or more therapeutic drugs for promoting healthy vessel wall, anti-thrombosis agents, and/or anti-blood clotting agents.

In another embodiment, the vascular stents comprising a dissolvable polymer further comprises targeting molecules, including receptor proteins, ligands, and/or differentiation markers. The vascular stents are useful for various clinical applications, including directing growth of cells of interest to different locations, promoting cellular activation, cellular de-differentiation, and/or cellular differentiation.

In another embodiment, the vascular stents comprising a dissolvable polymer further comprises angiogenesis inhibitors and/or chemotherapeutic drugs. Angiogenesis inhibitors and chemotherapeutic drugs inhibits angiogenesis, the proliferation of new blood vessels during tumor growth. The vascular stents can be placed within the lumen of vessels that vascularize tumors to pre-operatively promote tumor shrinkage, which may be critical for the treatment of brain tumors. Post-operatively, vascular stents can be placed within the lumen of large vessels that feed the tumor in order to optimize the delivery of chemotherapeutic and anti-angiogenic compounds. In another embodiment, a method for cancer treatment comprises placing a vascular stent within vessels, wherein the vascular stent releases a sufficient amount of chemotherapeutic and/or anti-angiogenic compounds to inhibit angiogenesis.

In another embodiment, a method for supporting the development of stem cells comprises placing a conduit comprising a dissolvable polymer within a tissue of interest, wherein the conduit comprises targeting molecules that can attract or recruit stem cells into the tissue of interest.

A dissolvable stent provides a number of advantages. During the initial stages of dissolution of the stent, the occluded vessel can repair and heal in the presence of locally infused growth factors, chemotherapeutic compounds, and anti-angiogenic compounds. At later stages of dissolution, the remains of the stent would completely dissolve away, leaving behind a healthy vessel. By avoiding traumatic and dangerous surgical intervention required by conventional non-dissolvable stents, the dissolvable stent would eliminate the need for continuous and costly maintenance/monitoring required by non-dissolvable stents. Furthermore, the flexibility of dissolvable stents can allow for stents to be inserted in complex spaces, such as branching points and bending sections of vessel architecture, unlike the rigid properties of non-dissolvable stents.

H. Exemplary Osmotic Pumps

FIG. 9 is an exemplary osmotic pump, as another embodiment. In FIG. 9A, an osmotic pump 900 is shown comprising a wick 910 deposited at the anterior end of the osmotic pump, and a solution 920 containing a compound of interest deposited at the posterior end. The osmotic pump 900 includes a subsection 925 at the anterior end that can be perforated to produce pores 912 that permit the inflow of bodily fluids, directly from a patient or obtained from a patient, into the osmotic pump 900. In FIG. 9B, an inflow of water 927 from the bodily fluids is shown, in which the water is immediately absorbed by the wick 910, which responds to the additional volume of water within the wick fibers by expanding 930 along the axis of the osmotic pump 900. The solution 920 from the posterior end of the osmotic pump is forced out 940 through an exit due to volume reduction and increased pressure within the interior compartment of the osmotic pump containing the solution of interest.

I. High Through-Put Methods and Devices for Sorting Cells of Interest

Figure 7:
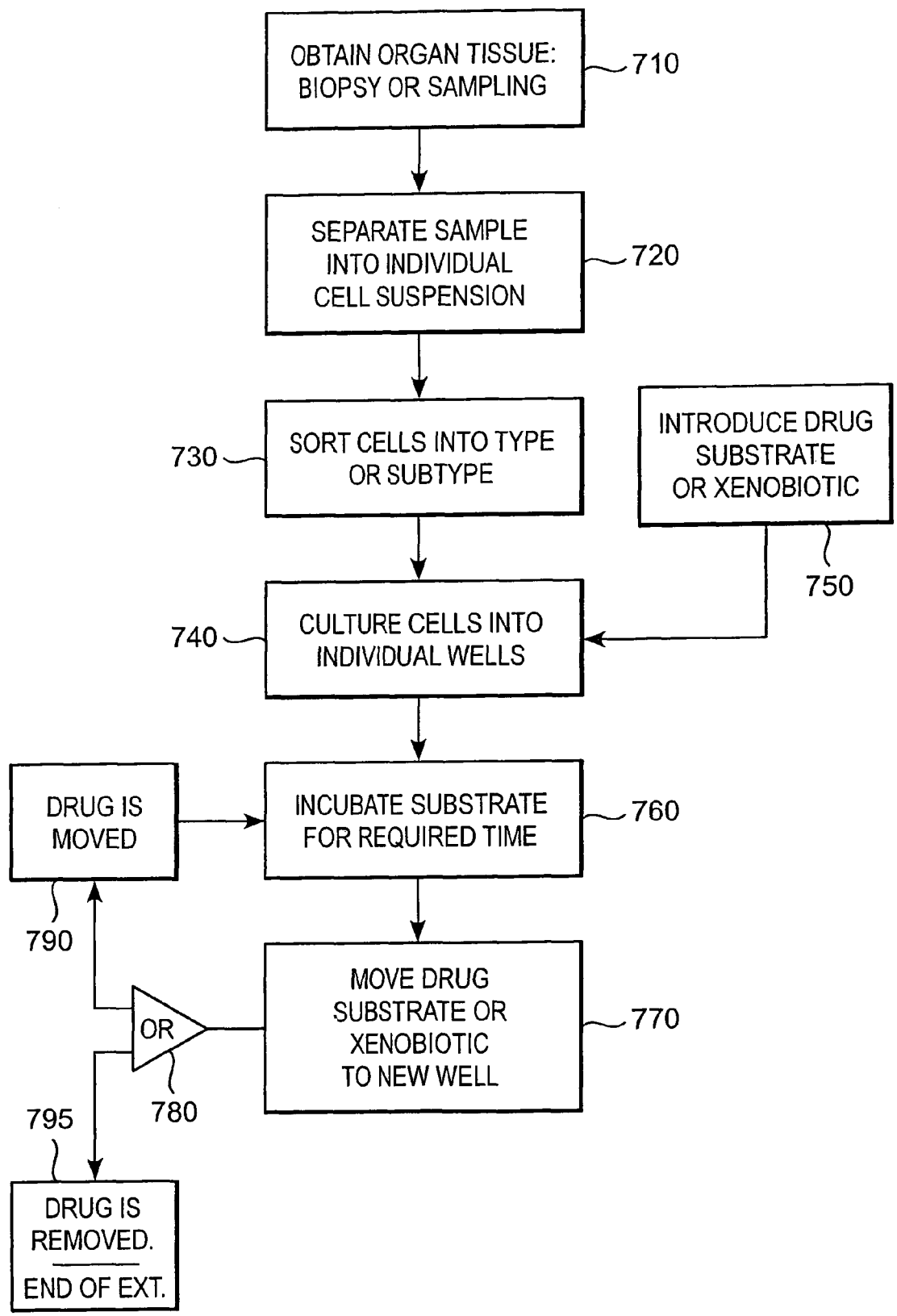
FIG. 7 is a process diagram for isolating, sorting, and fractionating subpopulations of cells from an organ of interest, and storing these fractions in discrete compartments.

FIG. 7 is a process diagram for isolating, sorting, and fractionating subpopulations of cells from an organ of interest, and storing these fractions in discrete compartments. In FIG. 7, the method comprises obtaining an organ by tissue biopsy 710; separating the organ into a suspension of individual cells 720; sorting individual cells into a batch of cells of identifiable cell type or cell subtype 730; culturing the batch of sorted cells into individual wells 740; introducing a drug, a substrate, or a xenobiotic into the batch of sorted cells 750; incubating the drug, substrate, or xenobiotic for a sufficient time to induce a biochemical effect on the batch of sorted cells 760; transferring the drug, substrate, or xenobiotic into a new well 770; and exposing the moved drug, substrate, or xenobiotic to a naïve batch of sorted cells and repeating the incubation step 760 until all batches of sorted cells have been evaluated. Subtypes of cells can be combined into various ratios within in vitro test chambers. By this process, metabolic products of one in vitro test chamber could be routed to another in vitro test chamber containing yet another cell type, cell subtype, of combination of cell types, or subtypes, that can be exposed to substrates and xenobiotics for further metabolic processing. By repeating the exposure step, this type of sequential metabolism represents an in vitro model of organs. This process can be implemented by the multi-chambered device illustrated in FIG. 8, as described below.

Figure 8:
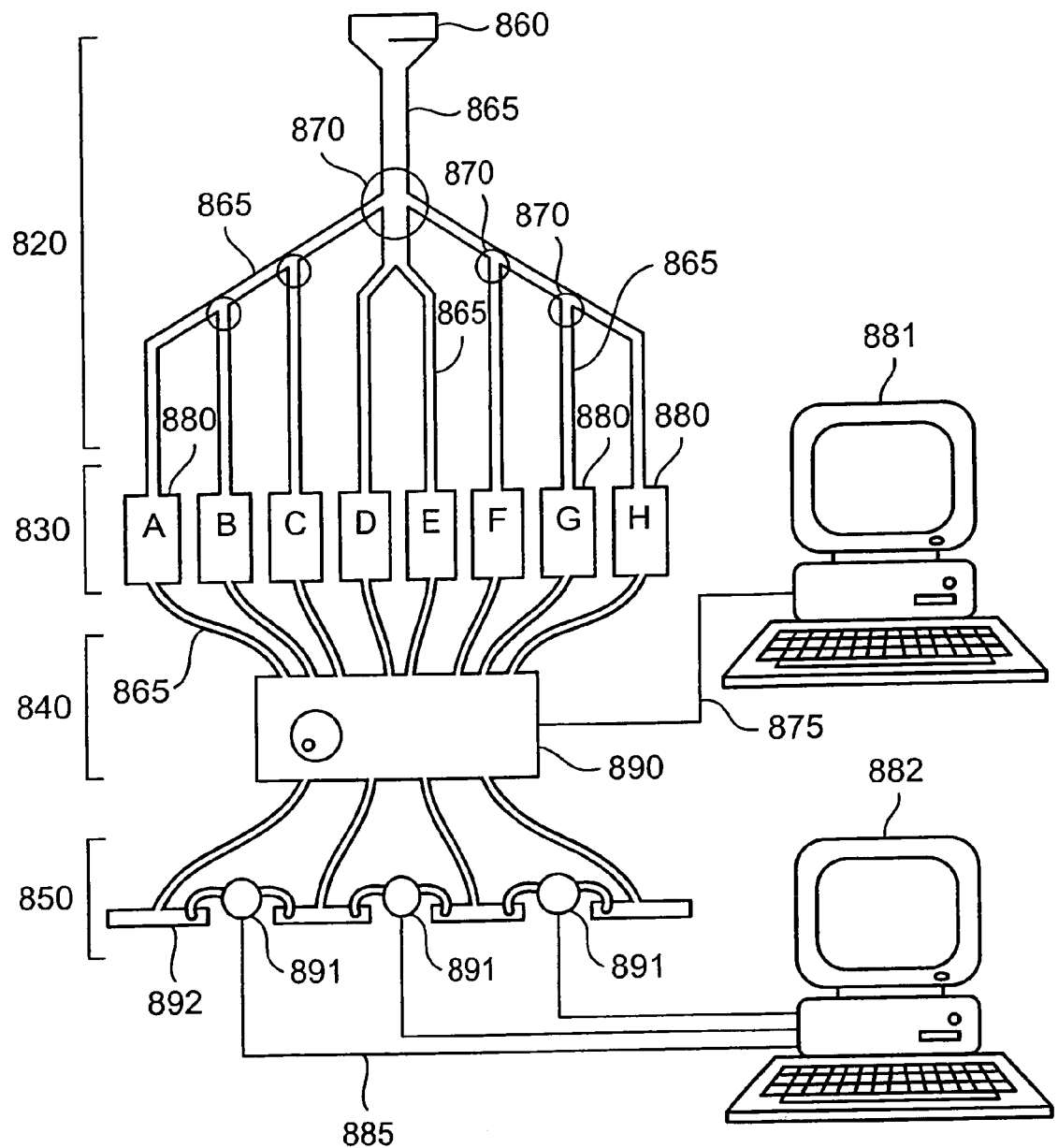
FIG. 8 illustrates a multi-chambered device for enabling high through-put method for sorting/fractionating subpopulations of cells derived from an organ, and storing sorted cells into discrete compartments.

FIG. 8 illustrates a multi-chambered device for enabling high through-put method for sorting/fractionating subpopulations of cells derived from an organ, and storing sorted cells into discrete compartments. In FIG. 8, a mixed population of cells can be deposited into a receptacle 860 of a cell-sorting system 820. The cells can be transferred from a collection tube 865 that further branches into various sorting channels. Cells can be sorted according various parameters (n), including differential size, differential electronegativity, differential expression of cell surface markers, or other criteria, for example, by utilizing filters 870 to distinguish cells exhibiting differential properties and by any active (e.g., flow cytometry) or passive (e.g., gel filtration) cell sorting processes known to persons skilled in the art. The sorted cells 830 can be deposited into individual storage vessels 880. The sorted cells can be transferred to a manifold system 840 that dispenses cells into individual wells 850 that can be configured for specific quantity and volume, by utilizing a computer system 881. Sorted cells can be deposited into microfluidic 850 or other systems that can incubate and support the growth of isolated cell populations. A computer system 882 can be utilized to control the rate of inflow of fluids and compounds between microwells by installation 885 of pumps 891.

The multi-chambered device of FIG. 8 is a microfluidic system(s) that enables high through-put sorting of cells into distinct flow chambers, based on flow characteristics of the cells. As another embodiment, a system of chambers can be controlled and constructed with microfluidics, in which sorted cells can be controllably re-combined into several mixed subpopulations. The flow characteristics varies according to various parameters, including cell size, cell shape, in-flow momentum characteristics, surface-adhesion properties, or other phenotypic expressions, and can be modulated by utilizing electrically- or magnetically-tagged cell markers, flow rate, gravity, or other parameters. High through-put, microfluidic system(s) can provide a series of connected flow chambers, in which each flow chamber contains immobilized cell populations, as pure or mixed cultures.

EXAMPLE

Utilization of Genetically-Engineered Lectins for Coating Implantable Devices as Targeting Molecules for Selecting Hematopoetic Cells In other embodiments, implantable devices can be coated with engineered lectin molecules as targeting molecules. Lectins are glycoproteins produced by vascular epithelium that can interact specifically and non-specifically with hematopoetic cells. The incorporation of engineered lectin molecules into implantable devices can improve the recruitment, sequestration, activation, and/or manipulation of a particular type of hematopoetic cells of interest, including T cells, monocytes, and various stem cells. Lectins can be produced by various genetic manipulation techniques known to persons skilled in the art, including site-directed mutagenesis, exon shuffling, domain swapping, chimeric gene construction, insertion and deletion mutagenesis, intron addition, and other changes that can alter 3D adhesive mechanism. Synthetically produced lectins are amenable to further modifications. In a preferred embodiment, synthetic lectins can be engineered to bind to specific cell-surface markers and cellular targets such as mesenchymal stem cells, ectodermal stem cells, or other exogenously cultured, manipulated, or engineered stem cells.

In another embodiment, synthetic lectins can be combined with ablative polymers for producing autorenewing (anti-fouling) adhesive coatings for implantable devices. In another embodiment, the combination of integrins, antibodies, and ablative polymers can be utilized for producing autorenewing (anti-fouling) adhesive coatings for implantable devices. In another embodiment, lectins can be used in combination with ablative polymers or hydrogels to impart a micro-supply of reagent (e.g., as a small reservoir, a droplet, or a blob) to cells contacting the surface. Integrins and antibodies in combination with ablative polymers can impart a micro-supply of reagents to cells contacting the surface. This micro-supply can contain one or more reagents, such as chemicals that force symmetric division (e.g., Xanthazine), chemicals that impart chemotactic signals, chemicals that inhibit signaling pathways activated by extraneous signals (e.g., p53 or NF-kB inhibitors).

As another embodiment, an ablative and intravascular device designed to release microscopic particles into the bloodstream can include molecules that recognize and bind to stem cell or cancer cell markers, including lectins, integrins, antibodies, and antibody fragments. Magnetic nanoparticles that can be controlled externally can be added to guide and retain stem cells at a target site in vivo. These particles can be made to include toxic chemicals that can kill a cancerous cell upon binding to the marker, molecules that facilitate the binding of stem cells to receptive pit sites in capillaries, such as bridging molecules and chemotactic agents.

Although several embodiments have been described in reference to specific or preferred embodiments, a number of variations and modifications of these embodiments will be apparent to persons skilled in the art. Such variations and modifications are to be considered within the purview and scope of the claims. Procedures, materials, and results may be adjusted if the procedures would be scaled up or if additional factors are taken into consideration. Thus, various modifications may be made without departing from the spirit and the scope of the invention. Accordingly, the invention is not limited except as by the appended claims.

We claim:

1. An implantable device comprising:
at least one chamber coated
with engineered lectins as a targeting molecule, and
with at least one non-lectin targeting molecule,
wherein the targeting molecule binds selectively to cell-type-specific markers expressed on the surface of hematopoetic cells, and
wherein the implantable device is a tube or a plurality of tubes, wherein the inner diameter of the tube is varied in a pattern along the length of the tube, wherein the thickness of the tube wall to form maximal inner diameter of the tube ranges from about 20 μM to about 1000 μM, the thickness of the tube wall to form minimal inner diameter of the tube ranges from about 20 μM to about 1000 μM, and the length of the tube between two sections of the tube with minimal inner diameters ranges from about 10 μM to about 2000 μM.

2. The implantable device of claim 1, wherein one or more of the targeting molecules is selected from the group consisting of: selectins, integrins, bacterial antigens, parasitic antigens, viral antigens, MHC Class I receptors, MHC Class II receptors, anti-HIV-capsid antibodies, antibodies having specificity for viral antigens, antibodies having specificity for bacterial antigens, antibodies having specificity for parasitic antigens, FASL, MHC Class I/antigen complex, and MHC Class II/antigen complex.

3. The implantable device of claim 1, wherein hematopoetic cells include T cells, monocytes, and stem cells.

4. The implantable device of claim 1, wherein the cell-type-specific markers include: T-cell receptors, T-cell-specific markers, monocyte-specific markers, and stem-cell-specific markers.

5. The implantable device of claim 1 further comprising: anti-viral drugs, RNAi, siRNA, gamma interferon, cytokines, differentiation factors, pharmaceutical drugs, chemotherapeutic compounds, signally peptides, or cytotoxic compounds.

6. A method for selectively recruiting, isolating, and/or activating cells of interest, the method comprising:
implanting the implantable device of claim 1 into a patient; and
providing sufficient time for the cells of interest to be recruited within the implantable device.

7. The method for vaccinating against pathogenic infection, the method comprising:
implanting within a host organism an implantable device comprising
MHC Class I molecules complexed with one or more antigen molecules derived from a pathogen; and
providing sufficient time for the host organism to become sensitized to the antigen in order to develop immunity against the pathogen,
wherein the implantable device is a tube or a plurality of tubes, wherein the inner diameter of the tube is varied in a pattern along the length of the tube, wherein the thickness of the tube wall to form maximal inner diameter of the tube ranges from about 20 μM to about 1000 μM, the thickness of the tube wall to form minimal inner diameter of the tube ranges from about 20 μM to about 1000 μM, and the length of the tube between two sections of the tube with minimal inner diameters ranges from about 10 μM to about 2000 μM.

8. An implantable device comprising:
a tube;
a primary coating layer on a surface of the tube comprising stem cell-specific targeting molecules that selectively capture, reduce cellular movement, and/or manipulate stem cell movement within the tube; and
a secondary coating layer deposited on a surface of the tube and/or superimposed on the primary coating layer comprising an agent affecting the activity of the recruited stem cell within the implantable device,
wherein the inner diameter of the tube is varied in a pattern along the length of the tube, wherein the thickness of the tube wall to form maximal inner diameter of the tube ranges from about 20 μM to about 1000 μM, the thickness of the tube wall to form minimal inner diameter of the tube ranges from about 20 μM to about 1000 μM, and the length of the tube between two sections of the tube with minimal inner diameters ranges from about 10 μM to about 2000 μM.

9. The implantable device of claim 8, wherein the agent of the secondary layer is selected from the group consisting of antiviral drugs, RNAi or siRNA molecules, gamma interferon, cytokines, and mixtures thereof.

* * * * *